(12) United States Patent
Roedle et al.

(10) Patent No.: US 10,695,493 B2
(45) Date of Patent: Jun. 30, 2020

(54) PEN-TYPE INJECTOR

(71) Applicant: VETTER PHARMA-FERTIGUNG GmbH & Co. KG, Ravensburg (DE)

(72) Inventors: Tilman Roedle, Wolfegg (DE); Tobias Kistler, Bergheim (DE); Sarah Kühnle, Friedrichshafen (DE); Roland Limbeck, Biberach (DE)

(73) Assignee: VETTER PHARMA-FERTIGUNG GMBH, Ravensburg (DE)

( * ) Notice: Subject to any disclaimer, the term of this patent is extended or adjusted under 35 U.S.C. 154(b) by 199 days.

(21) Appl. No.: 15/507,866

(22) PCT Filed: Sep. 3, 2015

(86) PCT No.: PCT/EP2015/070179
§ 371 (c)(1),
(2) Date: Mar. 1, 2017

(87) PCT Pub. No.: WO2016/034683
PCT Pub. Date: Mar. 10, 2016

(65) Prior Publication Data
US 2017/0281868 A1 Oct. 5, 2017

(30) Foreign Application Priority Data

Sep. 5, 2014 (DE) .................. 10 2014 217 773

(51) Int. Cl.
*A61M 5/20* (2006.01)
*A61M 5/24* (2006.01)
*A61M 5/315* (2006.01)

(52) U.S. Cl.
CPC ............... *A61M 5/20* (2013.01); *A61M 5/24* (2013.01); *A61M 5/2429* (2013.01);
(Continued)

(58) Field of Classification Search
CPC .... A61M 5/20; A61M 5/2448; A61M 5/2429; A61M 5/24; A61M 2005/31518;
(Continued)

(56) References Cited

U.S. PATENT DOCUMENTS 4,312,343 A 1/1982 LeVeen et al.
5,569,191 A 10/1996 Meyer
(Continued)

FOREIGN PATENT DOCUMENTS

EP 2050477 A1 4/2009
GB 2058228 A 4/1981
(Continued)

OTHER PUBLICATIONS

International Search Report and Written Opinion of the ISA for PCT/EP2015/070179, ISA/EP, Rijswijk, NL, dated Dec. 1, 2015.
(Continued)

*Primary Examiner* — Bhisma Mehta
*Assistant Examiner* — Hamza A Darb
(74) *Attorney, Agent, or Firm* — Stephen T. Olson; Harness, Dickey & Pierce, P.L.C.

(57) ABSTRACT

A pen includes a carpule having a longitudinal axis, a first end with a dispensing opening closable by a closure part, a second end via which at least one stopper can be inserted in the direction of the longitudinal axis, and an interior that is tightly closed by the closure part and the at least one stopper. A pen housing has a central axis, receives the carpule, and has a piston rod that interacts with the at least one stopper and a drive for moving the at least one stopper within the interior of the carpule, wherein the second end of the carpule can be inserted into the housing. The drive element moves the carpule into the housing in the direction of the longitudinal axis, which is arranged coaxially to the central axis of the housing, when the drive is activated; and in the process
(Continued)

the piston rod is held in a fixed position with respect to the longitudinal direction of the housing such that the piston rod, which is engaged in the second end of the carpule, moves the at least one stopper within the interior of the carpule in the direction of the first end of the carpule.

19 Claims, 1 Drawing Sheet

(52) U.S. Cl.
CPC ... *A61M 5/2448* (2013.01); *A61M 2005/2411* (2013.01); *A61M 2005/2444* (2013.01); *A61M 2005/2485* (2013.01); *A61M 2005/31518* (2013.01)

(58) Field of Classification Search
CPC .. A61M 2005/2485; A61M 2005/2411; A61M 2005/2444
See application file for complete search history.

(56) References Cited

U.S. PATENT DOCUMENTS

| | | | |
|---|---|---|---|
| 5,808,203 A | 9/1998 | Nolan, Jr. et al. | |
| 6,224,567 B1 | 5/2001 | Roser | |
| 6,645,177 B1 * | 11/2003 | Shearn | A61M 5/1456 604/155 |
| 9,108,004 B2 | 8/2015 | Rufer et al. | |
| 2010/0087799 A1 * | 4/2010 | Galbraith | A61M 5/2448 604/518 |
| 2011/0106018 A1 | 5/2011 | Rufer et al. | |
| 2012/0172817 A1 * | 7/2012 | Bruggemann | A61M 5/14566 604/218 |
| 2014/0243741 A1 * | 8/2014 | Kaufmann | A61M 5/2066 604/88 |

FOREIGN PATENT DOCUMENTS

| | | |
|---|---|---|
| GB | 2471304 A | 12/2010 |
| RU | 2203688 C2 | 5/2003 |
| WO | WO-94/13344 A1 | 6/1994 |
| WO | WO-2013/0144152 A1 | 10/2013 |
| WO | WO-2014/0118107 A1 | 8/2014 |

OTHER PUBLICATIONS

International Preliminary Report on Patentability and Written Opinion of the International Searching Authority regarding International Application No. PCT/EP2015/070179, dated Mar. 7, 2017.
Russian Search Report from the parallel Russian procedure 2017111193/14, dated Oct. 29, 2018, with English translation attached.
Office Action for parallel Japanese procedure 2010/523183.

* cited by examiner

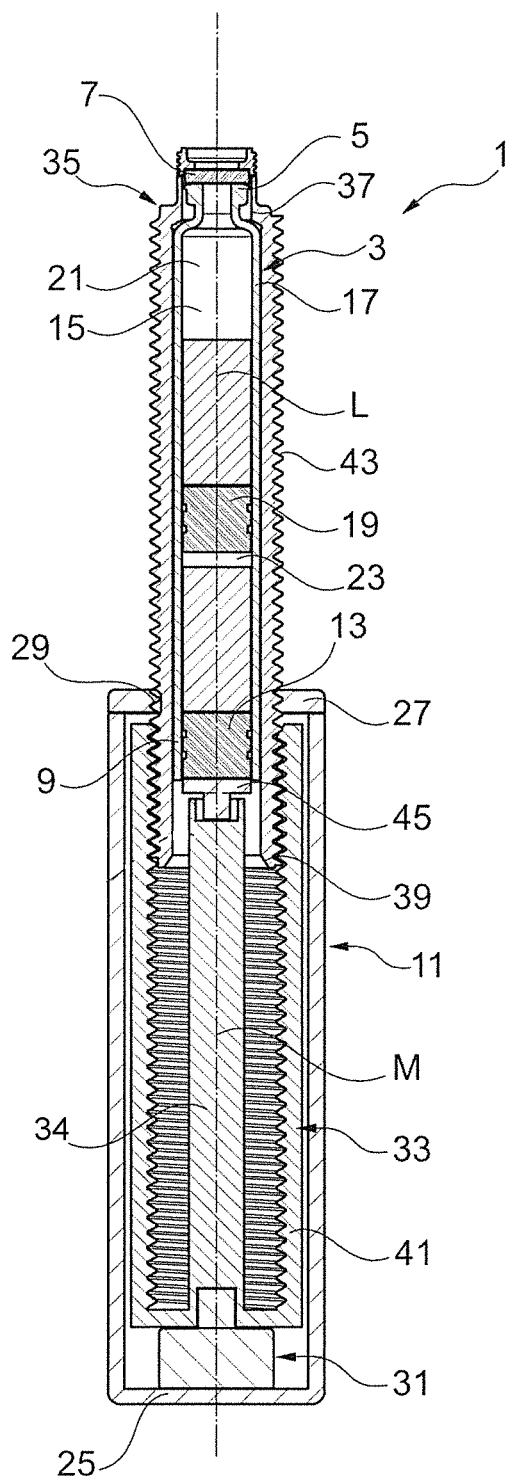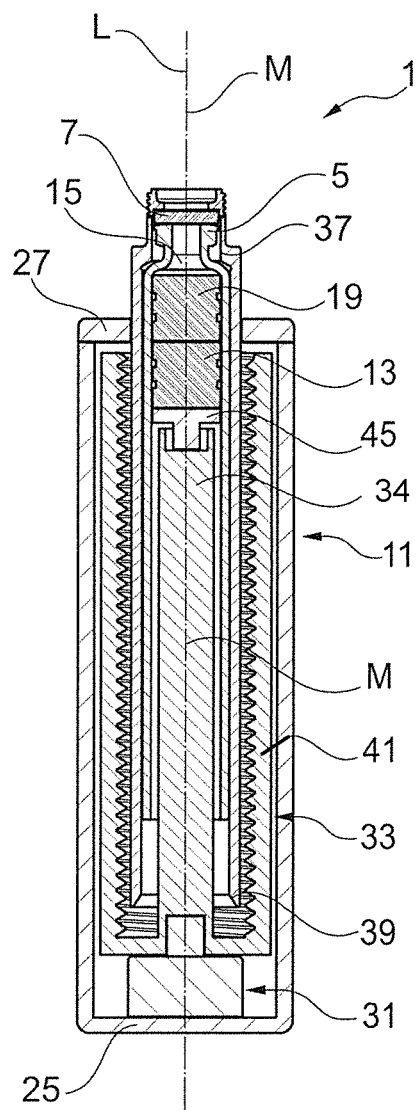
Fig. 1
Fig. 2

PEN-TYPE INJECTOR

CROSS-REFERENCE TO RELATED APPLICATIONS

This application is a 371 U.S. National Stage of International Application No. PCT/EP2015/070179, filed Sep. 3, 2015, which claims the benefit of and priority to German Patent Application No. DE 10 2014 217 773.1, filed Sep. 5, 2014. The disclosures of the above applications are incorporated herein by reference.

DESCRIPTION

Field

The invention relates to a pen having a carpule and having a housing that receives the pen.

BACKGROUND

Pens of the type discussed here are known. They are used for administering a medication to a patient. They are frequently designed such that the patient can perform the administration himself by means of the pen. The carpule for such pens has a chamber that is closed by a moveable stopper. By moving the stopper, the medication is driven out of the chamber and administered to a patient. This includes pens with a drive that is used to move the stopper within the chamber, preferably by a specific path, in order to administer a defined volume of a medication. It has been found that the size of the pen significantly limits the comfort of using such an application means. Therefore, pens that are designed relatively small are preferred. This has the drawback that this means only a limited quantity of a medication is available.

SUMMARY

The object of the invention is therefore to create a pen that can accommodate a relatively large volume of a medication.

For attaining this object, a pen of the aforesaid type is distinguished in that it is designed such that when the drive is actuated for moving the stopper within the interior space of the carpule, the carpule is driven into the housing of the pen. This leads to the pen becoming smaller—as seen in the direction of its longitudinal extension—with each application of a medication and it therefore is relatively large only in its initial position. Therefore, at least after the first application, but also, if the carpule is designed as a dual-chamber carpule, after the reconstruction of one of these substances present therein, the pen is shorter than conventional pens and may be carried unobtrusively by the user.

One exemplary embodiment of the pen is preferred that is distinguished in that it has a sleeve into which the carpule may be inserted. When the drive of the pen is actuated, the sleeve accommodating the carpule may be drawn into the housing of the pen so that it decreases in length. The sleeve has the advantage that the carpule is protected and is not as easily damaged.

One preferred exemplary embodiment of the pen is distinguished in that the drive has a drive element that is provided with at least one friction fit element. It acts on the carpule or on the sleeve such that the latter is moved into the interior space of the housing of the pen when a medication is discharged. This type of design is therefore particularly advantageous because the carpule and the sleeve do not have to be specially adapted in order to be driven into the housing by means of such a drive. The friction fit element may interact with any type of carpule and sleeve in order to cause the carpule to move.

In another preferred exemplary embodiment it is provided that the drive has a drive element that comprises at least a first positive fit element and that the carpule or the sleeve is equipped with at least one positive fit element. The two positive fit elements interact with one another such that when the drive is activated the carpule is moved into the interior space of the housing of the pen. Thus, in this exemplary embodiment, the exterior of the carpule or of the sleeve is specially molded in order to realize a second positive fit element that interacts with the first positive fit element. Thus the carpule and the sleeve must be matched to the first positive fit element. If the sleeve is equipped with at least one positive fit element, a conventional carpule may be inserted into it without the carpule then having to be matched to the drive element with the first positive fit element.

Particularly preferred is an exemplary embodiment in which the drive element is embodied as a threaded sleeve with at least one female thread segment. The threaded sleeve may be caused to rotate within the housing by the drive and in doing so may be borne such that it is held in a fixed position as seen in the longitudinal direction of the housing. Correspondingly, the outside of the carpule or of the sleeve is provided with at least one male thread segment that forms the second positive fit element and interacts with the female thread of the first positive fit element. The carpule and the sleeve are held rotation-fast in the housing so that when the drive element, that is the threaded sleeve, is activated, the carpule is drawn into the housing of the pen alone or with the sleeve.

Very particularly preferred is an exemplary embodiment of the pen that is distinguished in that at least one sensor is provided that detects the position of the carpule relative to the housing, especially the position of the at least one stopper relative to the piston rod. With this it is possible, when inserting the carpule, possibly together with a sleeve, to detect a defined initial position that may be used as a basis for ensuring that even the first application of a medication is provided with a precisely defined volume.

Additional embodiments result from the other subordinate claims.

BEST DESCRIPTION OF THE DRAWINGS

The invention is described in greater detail in the following using the drawings.

FIG. 1 is a longitudinal section of a pen in a first functional position; and,

FIG. 2 is a longitudinal section through the pen according to FIG. 1 in a second functional position.

DETAILED DESCRIPTION

FIG. 1 is a longitudinal section of a pen 1 with a carpule 3. The latter has a first end 5 that, in FIG. 1, is arranged at the top and is closed with a closure part 7. The opposing second end 9 of the carpule 3, disposed therebelow in FIG. 1, is disposed in the interior space of a housing 11 of the pen 1. The second end 9 of the carpule 3 may thus be inserted into the housing 11 in advance. The carpule 3 in this case is closed by a first stopper 13 inserted into the interior space of the former, so that an interior 15 of the carpule 3 is defined between the closure part 7 and the first stopper 13. This interior 15 is tightly closed by the closure part 7 and the first stopper 13.

A carpule 3 as may be used in conjunction with a pen 1 may be a known single chamber carpule that has a cylindrical body that is embodied continuously between the closure part 7 and the first stopper 13, depicted here, and that contains a medication to be administered.

Depicted here is a known dual chamber carpule that normally comprises a cylindrical base body 17, wherein the latter encloses the interior 15. In dual chamber carpules, in addition to the first stopper 13, a second stopper 19 is provided on the lower second end 9 and it divides the interior 15 into an upper sub-space 21 and a lower sub-space 23. Normally a first component of a medication, for instance a solvent, is housed in the lower sub-space 23, while a second component of the medication, for instance a lyophilizate, is disposed in the upper sub-space 21. Each sub-space 21, 23 may also contain a liquid, the liquids being mixed prior to use of the pen 1. For activating or reconstituting the lyophilizate, the first stopper 13 is moved upward inside the interior 15. This creates an overpressure in the lower sub-space 23, which leads to the second stopper 19 also being moved upward. Because of this, the second stopper 19 travels into the area of a bypass, not depicted here, so that the solvent can flow past the second piston 19 and thus travels for instance out of the lower sub-space 23 into the upper sub-space 21 and dissolves the lyophilizate. The carpule can be shaken to enhance the dissolution process. The structure and functioning or activation of a dual chamber carpule are known, so that this will not be discussed in greater detail here.

The pen 1 depicted here thus in particular has a carpule 13, whether a single chamber carpule or a dual chamber carpule, as depicted in FIG. 1, and at least one piston, in this case the first stopper 13. Dual chamber carpules are also provided with the second stopper 19 depicted here.

The exemplary embodiment of the pen 1 depicted in FIG. 1 has a housing 11 that is embodied essentially cylindrically and comprises here at its lower end a bottom 25 and at its upper end depicted in FIG. 1 a cover 27 with an opening 29 through which the carpule 3 may be inserted into the interior space of the housing 11.

A drive 31, which in this case has an energy supply that is not depicted, is disposed within the housing 11, preferably in the region of the bottom 25.

The drive 31 moves the carpule 3 into the interior space of the housing 11 when medication present in the interior 15 is to be administered. To make it possible to output the medication, the closure part 7 of the carpule 3 must be pierced with a conventional cannula.

What is critical is that when the carpule 3 is moved into the interior space of the housing 11, the first stopper 13 is moved into the interior 15 relative to the longitudinal axis L of the carpule 3 and the central axis M arranged coaxially thereto. In order to move the carpule 3 into the interior space of the housing 11, that is, in order to move the carpule 3 downward out of the illustrated upper first functional position depicted in FIG. 1, the drive 31 may have a drive element (not shown in FIG. 1) that interacts with the carpule 3 via friction or positive fit such that the latter is moved in the direction of its longitudinal axis L, and thus downward in the direction of the central axis M into the housing 11, when activated.

The pen 1 depicted here has a piston rod 34, arranged in the interior space of the housing 11 coaxially to the central axis M and to the longitudinal axis L, that, seen in the direction of the central axis M, is arranged in a fixed position in the housing 11. That is, the piston rod cannot be moved downward while the carpule 3 is being moved into the interior space of the housing 11. Because of this, the upper end 35 of the piston rod 34 moves relative to the carpule 3 while the latter is drawn into the housing 11. The first end 5 of the carpule 3 therefore moves toward the upper end 35 of the piston rod 34 so that the first stopper 13 in the interior 15 is also moved upward toward the first end 5 of the carpule 3.

In the exemplary embodiment of the pen 1 depicted in FIG. 1, the carpule 3 is arranged within a sleeve 36 that has a first opening 37 at the top for the first end 5 of the carpule 3, so that this first end 5 is accessible. The sleeve 36 also has a second opening 39 at its lower end, via which opening the at least one stopper of the carpule 3 is accessible, in this case the first stopper 13. For the basic function of the pen 1, which is designed to move the carpule 3 into the interior space of the housing 11 by means of the drive 31 and its drive element 33 into the interior space of the housing 11, it does not matter whether the drive element 33 acts directly on the carpule 3 or on the sleeve 36 that accommodates the carpule 3.

Nor is it important for the basic idea realized in the pen 1 here whether the drive 31 acts on the carpule 3 or sleeve 36 via a drive element 33, and to this end has a friction fit element, or whether the drive element 33 comprises at least one positive fit element that acts on at least a second positive fit element on the carpule 3 or sleeve 36 in order, when the drive 31 is activated, to move the carpule 3 into the interior space of the housing 11, possibly together with the sleeve 36. If the carpule 3 is arranged in the interior space of the sleeve 36, it is not necessary to match to the carpule 3 to the drive element 33, because the latter acts on the sleeve 36, moving it together with the carpule 3 into the interior space of the housing 11.

In the exemplary embodiment of the pen 1 depicted in FIG. 1, it is provided that the drive element 33 has a threaded sleeve 41 with a female thread that represents a first positive fit element. It is also preferably embodied here as continuous. However, it is certainly sufficient to provide at least one threaded segment extending longitudinally on the inside of the threaded sleeve 41. The threaded sleeve 41 may be caused to rotate by means of the drive 31. To this end, the former is rotatably borne in the interior space of the housing 11, but is housed in the housing 11 such that it is in a fixed position as seen in the direction of the central axis.

FIG. 1 depicts a pen 1 in which the carpule 3 is surrounded by a sleeve 36. Provided on its exterior is a second positive fit element that is embodied as a male thread 43.

When the drive 31 is activated, the drive element 33 embodied as threaded sleeve 41 is caused to rotate so that it rotates about the central axis M, but is held in a fixed position in the housing 11 relative to this axis. The female thread forming the first positive fit element of the drive element 33 interacts with the male thread 43 forming the second positive fit element on the outside of the sleeve 36 such that the sleeve 36, and thus also the carpule 3, are moved along the longitudinal axis L or the central axis M into the interior space of the housing 11. To permit the carpule 3 to move in its longitudinal direction when the drive element 33 is rotated, the sleeve 36 is arranged rotation-fast in the housing 11, wherein this rotation-fast bearing permits axial movement of the carpule 3 in the direction of its longitudinal axis L.

From these explanations it is clear that the second positive fit element, that is, a male thread, may also be realized directly on the exterior of the carpule 3. For realizing the principle by which the pen 1 functions, described herein, it is thus not necessary to use the carpule 3 together with a sleeve 36 that receives the same. However, it has been found that a sleeve 36 of the type addressed here is quite suitable for protecting the carpule 3 of the pen 1. In addition, when using such a sleeve 36, it is not necessary to embody a carpule 3 especially for use in conjunction with a pen 1 of the type addressed here. That is, it is possible to use normal carpules in a sleeve 36 addressed here in order to realize the pen 1.

It is particularly preferred that the drive element 33 and the piston rod 34 are embodied integrally. Thus, if the drive element 33 is caused to rotate using the drive 31, the piston rod 34 also rotates synchronously with the drive element 33 about the central axis M. Because of this, frictional forces that can result in drawbacks act between the upper end of the piston rod 34 and the first stopper 13. To prevent this, a rotation decoupling means 45 is preferably provided between the upper end of the piston rod 34 and the first stopper 13. This rotation decoupling means ensures that a rotation by the piston rod 34 is not transferred to the first stopper 13.

FIG. 2 depicts the pen 1 in a second functional position in which the entire carpule 3, which here is used together with the sleeve 36, is drawn into the interior space of the housing 11. Equivalent and functionally equivalent elements are provided with the same reference numbers, so that reference is made to the description of FIG. 1.

In this second functional position, the first stopper 13 has been moved as far as possible towards the first end 5 of the carpule 3, in this case the second stopper 19, as well, so that a medication present in the interior 15 is discharged completely.

When using the pen 1 described herein, during each application of the medication present in the interior 15, the carpule 3, in this case together with the sleeve 36, is moved into the interior space of the housing 11 so that the length of the pen 1 decreases with each application. The pen 1 is exactly as long as conventional pens only when it is in the freshly filled state. Its size decreases with each application during the reconstitution of a medication and during the administration of a medication present in the carpule 3 so that the pen 1 is easy to tuck away and can be carried around with nothing further. The smaller dimensions of the pen 1, as seen in the direction of the central axis M and longitudinal axis L, are thus extremely advantageous for a user.

Preferably provided in the pen described using FIGS. 1 and 2 is a sensor (not shown here) that detects the position of the carpule 3 relative to the housing 11, especially the position of the at least one stopper 13 relative to the piston rod 34. It is thus possible to ensure that before the first use of the pen 1 the piston rod 34 where necessary is positioned against the first stopper 13 via the preferably provided rotation decoupling means 45. During the first actuation of the pen 1, during which the drive 31 is activated and the carpule 3 is driven into the housing 11, the end of the piston rod 34 is in a defined initial position relative to the first stopper 13 in the interior space of the carpule 3 before the carpule 3 is moved. Thus a precisely defined quantity of a medication is dispensed from the interior 15 of the carpule 3.

The drive 31 has especially an electric motor. The latter is preferably provided with a sensor that permits the setting of a defined relative position between the piston rod 34 and the first stopper 13 and detects, for instance, the current consumed by the electric motor. The drive 31 may be deactivated as soon as the current consumed increases because the piston rod 34 where necessary is positioned via the rotation decoupling means 45 against the first stopper 13. Thus it is assured that a defined relative position is the result. This also ensures that a precisely defined volume of a medication is dispensed during the first activation of the pen 1.

The sensor mentioned here may thus be a sensor that detects the current consumed by the drive 31, or, for instance, an asynchronous counter, or even a sensor that detects the position of the upper end of the piston rod 34 or of the rotation decoupling means 45 relative to the first stopper 13 in a desired, known manner, whether mechanically or optically. In any case, a precise initial position of the upper end relative to the at least one stopper may be defined by means of a sensor described here, so that even the first volume of a medication dispensed by the pen 1 may be precisely predetermined. This assures safe use of this pen 1.

The invention claimed is:

1. A pen comprising:
 a carpule having a longitudinal axis, a first end with a dispensing opening closeable by a closure part, a second end receiving at least one stopper in a direction of the longitudinal axis, and an interior tightly closed by the closure part and the at least one stopper; and
 a housing having a central axis coaxial to the longitudinal axis, the housing receiving the carpule and having a piston rod and a drive, the piston rod interacting with the at least one stopper and arranged within the housing in a fixed position in a direction of the central axis of the housing, the drive for moving the at least one stopper within the interior of the carpule, the second end of the carpule inserted into the housing, the drive having a drive element that interacts with the carpule, the drive element operative to move the carpule into the housing in the direction of the longitudinal axis of the carpule when the drive is activated, and upon activation of the drive, the piston rod is fixedly held with respect to a longitudinal direction of the housing such that the piston rod, which is engaged in the second end of the carpule, moves the at least one stopper within the interior of the carpule in a direction of the first end of the carpule,
 wherein the drive element is a threaded sleeve having an interior surface with an interior thread, the threaded sleeve rotatable in the housing and held in a longitudinally fixed position in the housing while the sleeve is rotated,
 wherein an exterior surface of the carpule or a sleeve accommodating the carpule has an exterior thread engaged with the interior thread of the threaded sleeve, and
 wherein rotation of the drive element draws the carpule into the drive element to move the at least one stopper.

2. The pen according to claim 1, wherein the carpule is a dual-chamber carpule.

3. The pen according to claim 1, wherein the drive element has at least one friction fit element that acts on the carpule or on the sleeve accommodating the carpule in order to cause the carpule to move.

4. The pen according to claim 1, wherein the drive element has at least a first positive fit element and the carpule or the sleeve accommodating the carpule has at least a second positive fit element, and in that the first positive fit element and the second positive fit element interact such that when the drive is activated, the carpule is moved into the housing.

5. The pen according to claim 1, further comprising a rotation decoupling means between the piston rod and the at least one stopper.

6. The pen according to claim 1, wherein the drive has an electric motor.

7. The pen according to claim 6, wherein the drive has a sensor that detects a position of the piston rod relative to the at least one stopper.

8. The pen according to claim 1, further comprising a sensor for detecting a position of the carpule relative to the housing.

9. The pen of claim 8, wherein the sensor detects a position of the at least one stopper relative to the piston rod.

10. The pen according to claim 1, wherein the drive is located at a proximal end of the housing and the carpule extends from a distal end of the housing.

11. The pen according to claim 1, wherein the drive element and the piston rod are integrally formed and the drive element rotates synchronously with the piston rod within the housing about a common axis.

12. The pen according to claim 11, wherein the drive element includes a closed lower end, the piston rod upwardly extending from the closed lower end.

13. A pen comprising:
    a carpule having a longitudinal carpule axis, a first end with a dispensing opening closeable by a closure part, a second end receiving a stopper in a direction of the longitudinal carpule axis, and an interior tightly closed by the closure part and the stopper;
    a housing having a central housing axis coaxial to the longitudinal carpule axis, receiving the second end of the carpule;
    a piston rod interacting with the stopper and arranged within the housing in a fixed position in a direction of the central housing axis of the housing; and
    a drive for moving the stopper within the interior of the carpule, the drive having a drive element interacting with the carpule, the drive element operative to move the carpule into the housing in the direction of the longitudinal carpule axis of the carpule,
    wherein the piston rod is fixedly held with respect to a longitudinal direction of the housing such that the piston rod, which is engaged in the second end of the carpule, moves the stopper into the interior of the carpule, and
    wherein the drive element is a threaded sleeve having an interior surface with an interior thread, the threaded sleeve rotatable within the housing and held in a longitudinally fixed position within the housing while the sleeve is rotated,
    wherein an exterior of the carpule or a carpule sleeve accommodating the carpule has an exterior surface with an exterior thread engaged with the interior thread of the threaded sleeve, and the carpule or the carpule sleeve accommodating the carpule is arranged rotation-fast in the housing, and
    wherein rotation of the drive element draws the carpule into the drive element.

14. The pen according to claim 13, wherein the drive is located at a proximal end of the housing and the carpule extends from a distal end of the housing.

15. The pen according to claim 13, wherein rotation of the drive element operates to rotate the piston rod.

16. The pen according to claim 13, wherein the drive element and the piston rod are integrally formed and the drive element rotates synchronously with the piston rod within the housing about a common axis.

17. A pen comprising:
    a carpule having a longitudinal axis, a first end with a dispensing opening closeable by a closure part, a second end receiving at least one stopper in a direction of the longitudinal axis, and an interior tightly closed by the closure part and the at least one stopper; and
    a housing having a central axis coaxial to the longitudinal axis, the housing receiving the carpule and having a piston rod and a drive, the piston rod interacting with the at least one stopper, the piston rod rotatable within the housing and arranged within the housing in an axially fixed position, the drive for moving the at least one stopper within the interior of the carpule and toward the piston rod, the second end of the carpule inserted into the housing, the drive having a drive element with a threaded sleeve that intersects with the carpule, the threaded sleeve having an interior surface with an interior thread, the threaded sleeve rotatable in the housing to move the carpule into the housing in the direction of the longitudinal axis of the carpule upon rotation to engage the second end of the carpule with the piston rod so as to move the at least one stopper within the interior of the carpule, the threaded sleeve and the piston rod held in a longitudinally fixed position in the housing while the threaded sleeve is rotated,
    wherein the rotation of the threaded sleeve rotates the piston rod within with the housing while the piston rod is axially fixed.

18. The pen according to claim 17, wherein an exterior surface of the carpule or a sleeve accommodating the carpule has an exterior thread engaged with the interior thread of the threaded sleeve.

19. The pen according to claim 17, wherein the drive element and the piston rod are integrally formed and the drive element rotates synchronously with the piston rod within the housing about a common axis.

* * * * *